United States Patent [19]

Clem et al.

[11] Patent Number: 4,563,442

[45] Date of Patent: Jan. 7, 1986

[54] GLYCOPEPTIDE BIOCONVERSION PRODUCTS

[75] Inventors: Gladys M. Clem; LaVerne D. Boeck; Marie T. Anderson; Karl H. Michel, all of Indianapolis, Ind.

[73] Assignee: Eli Lilly and Company, Indianapolis, Ind.

[21] Appl. No.: 653,259

[22] Filed: Sep. 24, 1984

Related U.S. Application Data

[63] Continuation-in-part of Ser. No. 544,332, Oct. 21, 1983, abandoned.

[51] Int. Cl.$^4$ .................... A61K 37/00; A61K 35/00; C07C 103/52
[52] U.S. Cl. .......................... 514/9; 514/10; 514/11; 514/8; 260/112.5 R; 424/118
[58] Field of Search .................... 260/112.5 R; 514/8, 514/9, 10, 11; 424/118

[56] References Cited

U.S. PATENT DOCUMENTS

| | | | |
|---|---|---|---|
| 3,928,571 | 12/1975 | Raun | 424/118 |
| 3,952,095 | 4/1976 | Hamill et al. | 424/118 |
| 4,064,233 | 12/1977 | Hamill et al. | 424/118 |
| 4,115,552 | 9/1978 | Hamill et al. | 424/118 |
| 4,322,343 | 3/1982 | Debono | 260/112.5 R |
| 4,322,406 | 3/1982 | Debono et al. | 424/118 |
| 4,461,723 | 7/1984 | Hershberger et al. | 260/112.5 R |

OTHER PUBLICATIONS

M. Debono, "Structure and Activity of New Glycopeptide Antibiotics," oral presentation at 23rd Interscience Conference on Antimicrobial Agents and Chemotherapy, Las Vegas, Nevada, 1983, notes for relevant part of talk.

Primary Examiner—Delbert R. Phillips
Attorney, Agent, or Firm—Nancy J. Harrison; Arthur R. Whale

[57] ABSTRACT

New glycopeptide antibiotics of the formula:

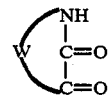

wherein

W is the remaining portion of a glycopeptide antibiotic selected from actaplanin factors $B_1$, $B_2$, $B_3$, $C_1$, $C_2$, $C_3$, $D_1$, $D_2$, $E_1$, G, K, L, M, N, O and actaplanin $\psi$aglycone, and salts thereof, particularly the pharmaceutically acceptable salts, are useful new antibiotics are active against gram-positive bacteria and increase feed-efficiency utilization and enhance milk production in ruminants.

14 Claims, No Drawings

GLYCOPEPTIDE BIOCONVERSION PRODUCTS

CROSS REFERENCE TO RELATED APPLICATION

This application is a continuation-in-part of copending application Ser. No. 544,332, filed Oct. 21, 1983, now abandoned.

SUMMARY OF THE INVENTION

This invention provides new glycopeptide antibiotics and processes for their preparation by bioconversion of the actaplanin factors using either of two new *Actinoplanes missouriensis* strains CUC 014 or CSV 558. The compounds produced by the bioconversion have the common formula 1:

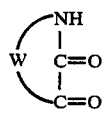

DETAILED DESCRIPTION OF THE INVENTION

This invention relates to the new glycopeptide antibiotics of formula 1. These antibiotics, are obtained by bioconversion of actaplanin (antibiotic A-4696) factors A, $B_1$, $B_2$, $B_3$, $C_1$, $C_2$, $C_3$, $D_1$, $D_2$, $E_1$, G, K, L, M, N, O and ψaglycone using either of two new *Actinoplanes missouriensis* strains, CUC 014 and CSV 558. Cultures CUC 014 and CSV 558 are the subject of a copending application of Charles L. Hershberger entitled NOVEL BIOCONVERTING MICROORGANISMS, Ser. No. 544,337, filed Oct. 21, 1983. *A. missouriensis* strains CUC 014 and CSV 558 have been deposited and made a part of the stock culture collection of the Northern Regional Research Center, Agricultural Research, North Central Region, 1815 North University Street, Peoria, Ill. 61604, from which they are available to the public under the accession numbers NRRL 15646 (CSV 558) and NRRL 15647 (CUC 014).

The glycopeptide antibiotics prepared by the process of this invention have the following formulas and individual designations:

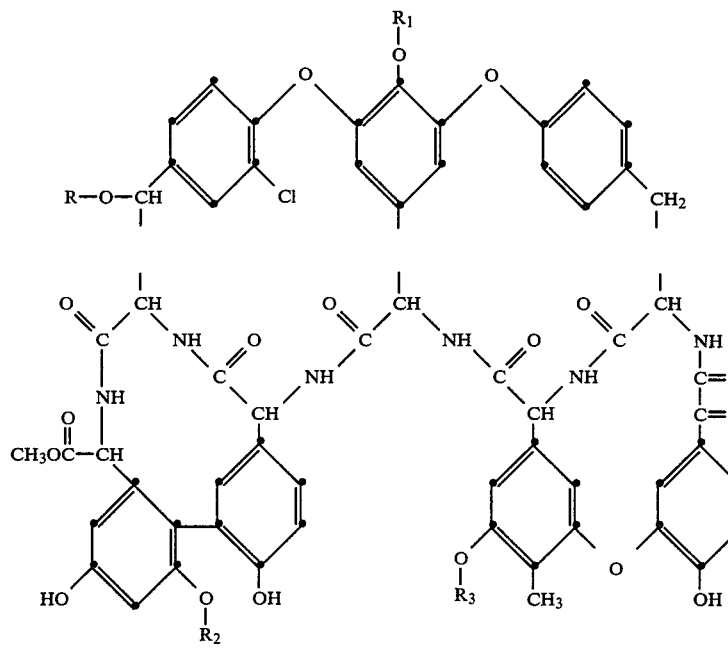

wherein W is the remainder of a glycopeptide antibiotic selected from actaplanin $B_1$, $B_2$, $B_3$, $C_1$, $C_2$, $C_3$, $D_1$, $D_2$, $E_1$, G, K, L, M, N, O and pseudo (ψ)aglycone which have the common structure 2

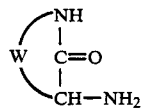

The formula 1 compounds and their salts, particularly the pharmaceutically acceptable salts, are useful new antibiotics. They are active against gram-positive bacteria and increase feed-efficiency utilization in animals and enhance milk production in ruminants.

| No. | Compound | $R_1$ | $R_2$ | $R_3$ |
|---|---|---|---|---|
| 1a | CUC/CSV | mannosyl-glucosyl | mannosyl | mannosyl |
| 1b | $B_1$/CSV | rhamnosyl-glucosyl | mannosyl | mannosyl |
| 1c | $B_2$/CSV | glucosyl | mannosyl | mannosyl |
| 1d | $B_3$/CSV | mannosyl-glucosyl | mannosyl | H |
| 1e | $C_1$/CSV | rhamnosyl-glucosyl | mannosyl | H |
| 1f | $C_2$/CSV | H | mannosyl | mannosyl |
| 1g | $C_3$/CSV | glucosyl | H | mannosyl |
| 1h | $D_1$/CSV | H | mannosyl | H |
| 1i | $D_2$/CSV | H | H | mannosyl |
| 1j | G/CSV | glucosyl | mannosyl | H |
| 1k | K/CSV | mannosyl-glucosyl | H | mannosyl |
| 1m | L/CSV | rhamnosyl-glucosyl | H | mannosyl |
| 1n | M/CSV | mannosyl-glucosyl | H | H |
| 1p | N/CSV | rhamnosyl-glucosyl | H | H |
| 1q | O/CSV | glucosyl | H | H |
| 1r | ψ/CSV | H | H | H |

Actaplanin (antibiotic A-4696) factors A and B are described by Hamill et al. in U.S. Pat. No. 4,115,552, issued Sept. 19, 1978. Actaplanin factors $B_1$, $B_2$, $B_3$, $C_{1a}$, $C_3$ and $E_1$ are described by Debono et al. in U.S. Pat. No. 4,322,406, issued Mar. 30, 1982 ($C_{1a}$ is now called $C_1$). The actaplanin pseudoaglycone is described by Debono in U.S. Pat. No. 4,029,769, issued Mar. 30, 1982. Actaplanin factor G is described by Hershberger et al. in U.S. Pat. No. 4,461,723, issued July 24, 1984; and actaplanin factors $C_{2a}$, $D_1$, $D_2$, K, L, M, N and O are described by Hunt et al. in a co-pending application, Ser. No. 488,967, filed Apr. 27, 1983 ($C_{2a}$ is now called $C_2$).

The actaplanin factors and pseudoaglycone have the structures shown in formulas 2a-2p:

PROCESS FOR ITS PRODUCTION, Ser. No. 544,338, filed Oct. 21, 1983, now U.S. Pat. No. 4,537,715

We have discovered that antibiotic CUC/CSV can be prepared by bioconversion of actaplanin factor A using either culture CUC 014 or culture CSV 558, and that the other actaplanin factors can be bioconverted in the same manner to give similarly modified products, i.e. the compounds of formula 1.

It was subsequently discovered that antibiotic CUC/CSV is a minor factor produced by the actaplanin-producing culture *A. missouriensis* ATCC 31683. Antibiotic CUC/CSV was then assigned the designation factor "J" of the A-4696 (actaplanin) complex.

Molloy and Debono also discovered that antibiotic

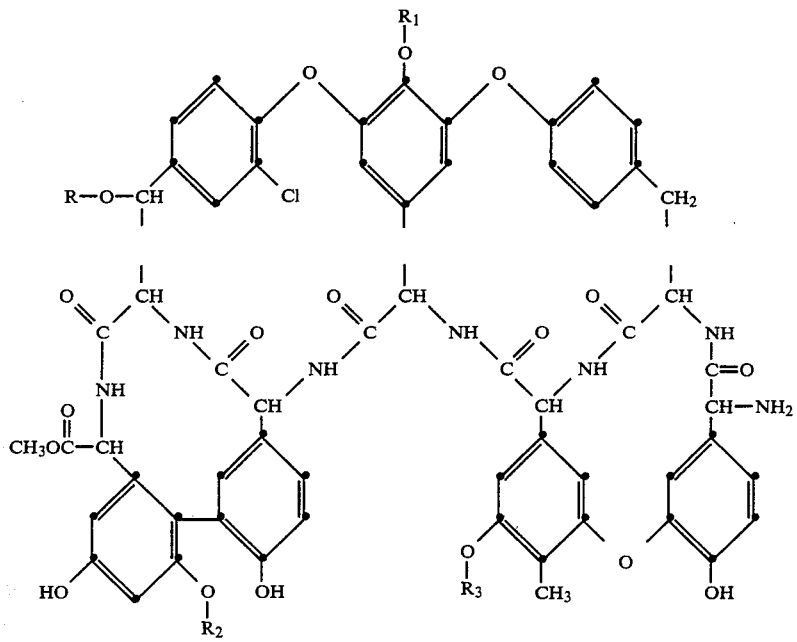

2

| Formula | Actaplanin | $R_1$ | $R_2$ | $R_3$ |
|---|---|---|---|---|
| 2a | A | mannosyl-glucosyl | mannosyl | mannosyl |
| 2b | $B_1$ | rhamnosyl-glucosyl | mannosyl | mannosyl |
| 2c | $B_2$ | glucosyl | mannosyl | mannosyl |
| 2d | $B_3$ | mannosyl-glucosyl | mannosyl | H |
| 2e | $C_1$ | rhamnosyl-glucosyl | mannosyl | H |
| 2f | $C_2$ | H | mannosyl | mannosyl |
| 2g | $C_3$ | glucosyl | H | mannosyl |
| 2h | $D_1$ | H | mannosyl | H |
| 2i | $D_2$ | H | H | mannosyl |
| 2j | G | glucosyl | mannosyl | H |
| 2k | K | mannosyl-glucosyl | H | mannosyl |
| 2m | L | rhamnosyl-glucosyl | H | mannosyl |
| 2n | M | mannosyl-glucosyl | H | H |
| 2o | N | rhamnosyl-glucosyl | H | H |
| 2p | O | glucosyl | H | H |
| 2q | ψaglycone | H | H | H |

It was earlier discovered that antibiotic CUC/CSV was produced by cosynthesis of the two *A. missouriensis* strains CUC 014 and CSV 558. Antibiotic CUC/CSV has formula 1a. Antibiotic CUC/CSV and the method of preparing it by cosynthesis of strains CUC 014 and CSV 558 are described in a copending application by LaVerne D. Boeck, Gladys M. Clem, Charles L. Hershberger, Marie T. Anderson and Karl H. Michel entitled GLYCOPEPTIDE ANTIBIOTIC CUC/CSV AND CUC/CSV and the formula 1 compounds can be prepared chemically by oxidative deamination of the parent antibiotics and have described this in their copending application entitled NOVEL GLYCOPEPTIDE DERIVATIVES, Ser. No. 544,339 filed Oct. 21, 1983.

In another aspect, this invention relates to methods of treating certain infections with, methods of increasing feed-utilization efficiency with, a method of improving milk production in lactating ruminants with, and pharmaceutical compositions comprising, a formula 1 compound or a pharmaceutically acceptable salt thereof together with a suitable carrier.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

The formula 1 compounds form salts, particularly acid addition salts. These acid addition salts are also useful as antibiotics and are a part of this invention. In another aspect, such salts are useful as intermediates, for example, for separating and purifying the derivatives.

Representative suitable salts include those salts formed by standard reaction with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicyclic, methanesulfonic, benzenesulfonic, sorbic, picric, benzoic, cinnamic, and like acids.

Pharmaceutically acceptable acid addition salts are an especially preferred group of salts of this invention.

In the process provided by this invention, antibiotic CUC/CSV or a formula 1 compound is produced by bioconversion of the corresponding actaplanin factor using either of the *A. missouriensis* strains CSV 558 (NRRL 15646) and CUC 014 (NRRL 15647) under submerged aerobic conditions in a suitable culture medium until substantial conversion to the desired product has occurred.

As will be appreciated by those in the art, the culture media used to grow the bioconverting *A. missouriensis* strains can be any one of a number of media (see, for example, U.S. Pat. No. 4,322,406 for a description of the media variations useful for the parent *A. missouriensis* ATCC 31683 strain). When carrying out the bioconversion, the appropriate substrate can be added to the growing fermentation or can be included in the medium after sterilization, but before inoculation.

The bioconversion can be followed during the fermentation by testing samples of the broth by thin-layer chromatography (TLC) as described in Example 1, Sect. D.

Following its production under submerged aerobic fermentation conditions, antibiotic CUC/CSV or the formula 1 compound can be recovered from the fermentation medium by methods recognized in the art, e.g. adsorptive and extractive procedures.

Alternatively, the culture solids, including medium constituents and mycelium, can be used without extraction or separation, but preferably after removal of water, as a source of antibiotic CUC/CSV or the formula 1 compound. For example, after production of antibiotic CUC/CSV, the whole fermentation broth can be dried by lyophilization, by drum-drying, or by azeotropic distillation and drying. The dried whole broth can then be mixed directly into feed premix.

Antibiotic CUC/CSV and the formula 1 compounds inhibit the growth of pathogenic bacteria, especially gram-positive bacteria. Table I summarizes the minimal and inhibitory concentrations (MIC's) at which CUC/CSV inhibits certain organisms, as determined by standard agar-dilution assays.

TABLE I

| | In Vitro Activity of Bioconversion Products | |
|---|---|---|
| | MIC (mcg/ml) | |
| Organism | CUC/CSV | B$_2$ Product |
| *Staphylococcus aureus* NRRL B313 | 8 | 4 |
| *Staphylococcus aureus* V41 | 8 | 8 |
| *Staphylococcus aureus* X400 | 16 | 16 |
| *Staphylococcus aureus* S13E | 8 | 4 |
| *Staphylococcus epidermidis* EPI1 | 16 | 16 |
| *Staphylococcus epidermidis* 222 | 8 | 2 |
| *Streptococcus pyogenes* C203 | —[a] | 1 |
| *Streptococcus pneumoniae* Park 1 | 0.5 | 1 |

TABLE I-continued

| | In Vitro Activity of Bioconversion Products | |
|---|---|---|
| | MIC (mcg/ml) | |
| Organism | CUC/CSV | B$_2$ Product |
| *Streptococcus faecium* ATCC 9790 | 4 | 4 |
| *Streptococcus sp.* group D 9960 | 4 | 4 |

[a]Not tested

Antibiotic CUC/CSV also inhibits the growth of anaerobic bacteria. Table II summarizes the susceptibility of various anaerobic isolates to CUC/CSV.

TABLE II

| Susceptibility of Anaerobic Bacterial Isolates to CUC/CSV | |
|---|---|
| Anaerobic Bacteria | MIC (μg/ml)[a] |
| *Clostridium difficile* 2994 | 1 |
| *Clostridium perfringens* 81 | 4 |
| *Clostridium septicum* 1128 | 4 |
| *Eubacterium aerofaciens* 1235 | 2 |
| *Peptococcus asaccharolyticus* 1302 | 4 |
| *Peptococcus prevoti* 1281 | 8 |
| *Peptostreptococcus anaerobius* 1428 | 2 |
| *Peptostreptococcus intermedium* 1264 | 4 |
| *Propionibacterium acnes* 79 | 1 |
| *Bacteroides fragilis* 111 | >128 |
| *Bacteroides fragilis* 1877 | >128 |
| *Bacteroides fragilis* 1936B | >128 |
| *Bacteroides thetaiotaomicron* 1438 | >128 |
| *Bacteroides melaninogenicus* 1856/28 | >128 |
| *Bacteroides melaninogenicus* 2736 | 16 |
| *Bacteroides vulgatis* 1211 | >128 |
| *Bacteroides corrodens* 1874 | >128 |
| *Fusobacterium symbiosum* 1470 | >128 |
| *Fusobacterium necrophorum* 6054A | 2 |

[a]MIC's were determined by the agar-dilution method; endpoints were read after 24-hours incubation.

CUC/CSV has also shown in vivo antimicrobial activity against experimentally-induced bacterial infections. When two doses of test compound were administered to experimentally infected mice, the activity observed was measured as an ED$_{50}$ value [effective dose in mg/kg to protect 50% of the test animals: see Warren Wick et al., *J. Bacteriol.* 81, 233–235 (1961)]. ED$_{50}$ values observed for CUC/CSV are given in Table III.

TABLE III

| ED$_{50}$ Values for CUC/CSV in Mice | |
|---|---|
| Infecting Organism | ED$_{50}$ (mg/kg/2)[a] |
| *Staphylococcus aureus* | 1.59 |
| *Streptococcus pyogenes* | 1.09 |
| *Streptococcus pneumoniae* | 0.84 |

This invention also relates to a method of controlling bacterial infections. In carrying out the method of this invention, an effective amount of a formula 1 compound is administered parenterally or orally to an infected or susceptible warm-blooded animal. The compound can also be administered by insufflation, i.e. by blowing the compound, in the form of a medicated dust, into an enclosed space or room wherein the animals or poultry are held. The animals or poultry breathe the medicated dust present in the air; the medicated dust is also taken into the body through the eyes (a process called intraocular injection).

The dose which is effective to control the infection will vary with the severity of the infection and the age, weight, and condition of the animal. The total dose required for protection parenterally will generally, however, be in the range of from about 0.1 to about 100 mg/kg and preferably will be in the range of from about 0.5 to about 50 mg/kg. The dose required for oral administration will generally be in the range of from 1 to about 300 mg/kg and preferably will be in the range of from about 1 to about 100 mg/kg. Suitable dosage regiments can be constructed.

Often the most practical way to administer the compounds is by formulation into the feed supply or drinking water. A variety of feeds, including the common dry feeds, liquid feeds, and pelleted feeds, may be used.

In another aspect, this invention relates to compositions useful for the control of bacterial infections. These compositions comprise a formula 1 compound together with a suitable vehicle. Compositions may be formulated for parenteral or oral administration by methods recognized in the pharmaceutical art.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In another embodiment, this invention relates to methods of increasing feed-utilization efficiency and promoting growth rates in poultry, swine, sheep and cattle and of enhancing milk production in lactating ruminants. For increasing feed utilization efficiency and promoting growth, a formula 1 compound is administered orally in a suitable feed in an amount of from about 2 to about 200 grams per ton of total feed. For enhancing milk production in lactating ruminants, oral administration of a daily amount of from about 0.01 to about 10 mg/kg of body weight (or about 100 to about 1600 mg/ruminant/day) is suggested.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing a formula 1 compound.

The following examples illustrate this invention.

EXAMPLE 1

Preparation of Antibiotic CUC/CSV by Bioconversion of Actaplanin Factor A using Culture CUC 014 or CSV 558

A. Shake-Flask Fermentation of Cultures CUC 014 and CSV 558

A lyophilized pellet of *Antinoplanes missouriensis* strain CUC 014 (NRRL 15647) or strain CSV 558 (NRRL 15646) is dissolved in 1–2 ml of sterilized water. This suspension is used to inoculate an agar slant having the following composition:

| Ingredient | Amount (%) |
| --- | --- |
| Precooked Oatmeal | 6.0 |
| Yeast | 0.25 |
| $K_2HPO_4$ | 0.1 |
| Czapek Mineral Stock[a] | 0.5 |
| Agar[b] | 2.5 |
| Deionized $H_2O$ | q.s. to 100% |
| Unadjusted pH = 6.2; adjust to pH 7.3 with 5N NaOH; after sterilization pH = 6.7. | |
| KCl | 10.0 |
| $MgSO_4.7H_2O$ | 10.0 |
| $FeSO_4.7H_2O$ | 0.2 (dissolved in 2 ml of Conc. HCl) |
| Deionized water | q.s. to 100% |

[a]Czapek Mineral Stock
[b]Difco Laboratories

The inoculated slant is incubated at 30° C. for about eight to ten days. The mature slant culture is scraped with the serrated edge of a sterile loop to mascerate and loosen the mycelial mat. About one-fourth of the loosened mat is used to inoculate 50 ml of a vegetative medium having the following composition:

| Ingredient | Amount (%) |
| --- | --- |
| Glucose | 2.0 |
| Tryptone[a] | 0.5 |
| Yeast Extract | 0.5 |
| Tap $H_2O$ | q.s. to 100% |
| Before sterilization, pH = 6.5; adjust to pH 7.2 with 5 N NaOH; after sterilization, pH = 6.9; | |

[a]Bacto Tryptone, Difco

The inoculated vegetative medium is incubated in a 250-ml Erlenmeyer flask at 30° C. for about 72 hours on a rotary shaker with a two-inch throw at 250 RPM.

Vegetative cultures can be initiated with agar-slant cultures, with lyophilized pellets of the culture (one lyophile per 50 ml of media in a 250-ml flask) and with cultures preserved in liquid nitrogen (0.8% inoculum).

Incubated vegetative medium (5%, volume/volume) is used to inoculate 50 ml of a production medium having the following composition:

| Ingredient | Amount (%) |
| --- | --- |
| Glucose | 2.5 |
| Corn Starch | 3.5 |
| Blackstrap Molasses | 1.5 |
| Glycerol | 1.5 |
| Yeast | 2.0 |
| $K_2HPO_4$ | 0.05 |
| $(NH_4)_2SO_4$ | 0.025 |
| $CaCO_3$ | 0.2 |
| Tap $H_2O$ | q.s. to 100% |
| Before sterilization pH = 6.5; adjust to 6.8; after sterilization pH = 6.5. | |

The inoculated production medium is incubated in a 250-ml Erlenmeyer flask at 30° C. for 72 hours on a 2-inch rotary shaker at 250 RPM.

B. The Bioconversion

Actaplanin factor A (100 mg) was dissolved in water, sterilized by filtration, and added (final conc. of 0.3 mg/ml) to a five-day-old, one-liter fermentation of the convertor culture *A. missouriensis* CSV 558 (NRRL 15646). The fermentation was incubated an additional 48 hrs. The pH of the whole broth was adjusted to 10.5 with NaOH; the broth was centrifuged, and the centrate was neturalized with HCl.

C. Isolation of CUC/CSV

A bioconversion was carried out using the procedure of Sect. B. The broth was removed by filtration, and the mycelia were extracted with water a pH 10.5. This extract (550 ml) was purified over a column packed with 100 ml of HP-20, washed with water, then eluted with a gradient of MeOH:$H_2O$ to MeOH. Fractions were combined to give a lyophilized crude product (190 mg). A portion of this product (100 mg), dissolved in 5 ml of $CH_3CN$:pyrOAc (36:64) at pH 3.6, was applied to a 300-ml glass column packed with Lichroprep RP-8 resin (25–40 μm). The column was eluted with $CH_3CN$:0.05% pyrOAc (1:4) at pH 3.6 at a flow rate of 8 ml/min. Product was detected by UV absorbance at 280 nm, by *B. subtilis* bioassay and by analytical HPLC. Fractions containing the desired activity were combined, adjusted to pH 6.5 with N NaOH then concentrated to remove $CH_3CN$. The resulting aqueous solution (50 ml) was applied to a 40-ml column filled with 12 ml of LP1-C18 resin (see U.S. Pat. No. 4,293,482, Example 7) in water. The column was washed with water (100 ml) to remove the salt, and the active material was eluted with $CH_3CH$:$H_2O$ (7:3). The eluate was concentrated and lyophilized to give 10 mg of purified antibiotic CUC/CSV.

D. Assay for Antibiotic CUC/CSV

Whole broth (adjusted to pH 10.5) is centrifuged. The supernatant is readjusted to pH 7.0. Samples thus prepared are assayed by a *Bacillus subtilis* plate assay and by thin-layer chromatography using silica-gel plates (Merck, pre-coated plastic sheets; silica gel 60, without fluorescent indicator) and an acetone:water:ammonia (160:40:1) solvent system. Detection was by bioautography using *B. subtilis* in a minimal growth medium and incubating plates at 37° C. for about 18 hours.

CUC/CSV has the following characteristics:

| | Elemental Analysis | |
| --- | --- | --- |
| | Calc.[a] | Found |
| C-90 | 49.46 | 49.28 |
| H-98 | 5.63 | 4.35 |
| N-7 | 4.49 | 4.55 |
| O-41 | 38.80 | 39.82 (by difference) |
| Cl-1 | 1.62 | 2.00 |

For $C_{90}H_{98}N_7O_{41}Cl.12H_2O$

Ultraviolet Absorption (in methanol):
 $\lambda_{max}$ 278 nm, acid ($\epsilon \sim 17,000$)
 $\lambda_{max}$ 277 nm, 361 nm, neutral ($\epsilon \sim 18,500, 9,000$)
 $\lambda_{max}$ 295 nm, 340 nm, base ($\epsilon \sim 21,000, 14,500$)
Calculated on a molecular weight of 1200. The compound shows end-absorption at 230 nm.
Solubility: soluble in dimethyl sulfoxide, dimethylformamide, acetonitrile:water, and alcohol:water mixtures.
Mass Spectrometry (Fast Atom Bombardment): FAB MS indicates a molecular weight of 1968.

EXAMPLE 2

Preparation of CUC/CSV by Bioconversion of Actaplanin Factor A with Culture CUC 014

Following the procedure of Example 1, but using culture CUC 014 (NRRL 15647) instead of culture CSV 558, actaplanin factor A is converted to antibiotic CUC/CSV.

EXAMPLE 3

Analytical HPLC System For Antibiotic CUC/CSV

Column: 4.6-×250-mm stainless steel
Packing: Shandon ODS Hypersil-5 micron
Solvent: $CH_3CN$:0.05M $KH_2PO_4$ adjusted to pH 3.2 with $H_3PO_4$ (21:79)
Flow Rate: 1.0 ml/min.
Detection: UV at 220 nm
Chart speed: 20 cm/hr.
Retention time: 9.3 minutes

EXAMPLE 4

Preparation of A4696 $B_2$ Conversion Product (Compound 2c)

Using the procedure of Example 1, Actaplanin (A4696) factor $B_2$ (200 mg) was added to a growing culture of the *A. missouriensis* CSV 558 convertor culture. Bioconversion was followed TLC. When bioconversion was complete, the broth was separated by filtration. The separated mycelia were extracted with water at pH 10.5 (adjusted with NaOH). This extract was purified over a column packed with HP-20 resin (185 ml) as described in Example 1 to give 313 mg of a lyophilized product. A portion of this product (160 mg) was applied to a glass column packed with 170 ml of Fractogel TSK HW-40S resin (32-63 micron, E. Merck, Darmstadt, Germany) and run at a flow rate of 3 ml/min, using 3.3 L. of water, then 700 ml of MeOH:$H_2O$ (1:1). The product was in the MeOH:$H_2O$ fractions; these were concentrated and lyophilized and then combined with a similarly prepared product. The combined product was re-chromatographed on the same resin, using the following stepwise MeOH:$H_2O$ gradient:150 ml of (1:3); 350 ml of (2:3); 550 ml of (3:2); and 470 ml of (4:1). Fractions were monitored by analytical HPLC, and fractions containing the desired product were combined, concentrated and lyophilized to give 20.3 mg of A4696 $B_2$ bioconversion product.

EXAMPLE 5

Preparation of A4696 $C_1$ Conversion Product (Compound 1e)

Using a procedure like that of Example 1, actaplanin factor $C_1$ (240 mg) was added to a growing culture of the *A. missouriensis* CSV 558 convertor culture. After bioconversion was complete, the broth was filtered, and the separated mycelia were extracted with $H_2O$ at pH 10.5 (adjusted with NaOH). This extract, (650 ml) was purified over a column packed with 100 ml of HP-20 resin as described in Example 1 to give 187 mg of lyophilized product.

This product (185 mg) was dissolved in 8 ml of $MeOH:H_2O$ (7:3), filtered, and applied to a 170-ml glass column packed with Fractogel TSK HW-40S resin. The column was run in $MeOH:H_2O$ (2:3) at a flow rate of 2 ml/min. Fractions were monitored by padding on *B. subtilis* and by analytical HPLC. Fractions containing the desired product were combined and applied to a 300 ml column packed with Lichroprep RP-8 resin (25–40 micron) and run in $CH_3CN:0.05\%$ aqueous pyrOAc (1:4) adjusted to pH 3.5. Fractions were monitored by analytical HPLC; and fractions containing the product were combined, adjusted to pH 6.5 and concentrated. This aqueous solution was applied to a column packed with 60 ml of HP-20 resin, and the column was washed with $H_2O$ to remove salt. The active material was eluted with $CH_3CN:H_2O$ (4:1), and the eluate was concentrated and lyophilized to give 5.9 mg of A4696 $C_1$ conversion product.

We claim:

1. A compound of the formula:

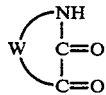

wherein

W is the remaining portion of a glycopeptide antibiotic selected from actaplanin factors $B_1$, $B_2$, $B_3$, $C_1$, $C_2$, $C_3$, $D_1$, $D_2$, $E_1$, G, K, L, M, N, O and actaplanin ψaglycone, each of which has the structure:

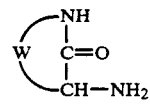

or a salt thereof.

2. The compound of claim 1 wherein the glycopeptide antibiotic is actaplanin factor $B_2$.

3. The compound of claim 1 wherein the glycopeptide antibiotic is actaplanin factor $C_1$.

4. The compound of claim 1 wherein the glycopeptide antibiotic is actaplanin G.

5. The compound of claim 1 wherein the glycopeptide antibiotic is actaplanin ψaglycone.

6. The salts of claim 1 which are acid addition salts.

7. The salts of claim 1 which are pharmaceutically acceptable.

8. A pharmaceutical composition which comprises a compound of claim 1, or a pharmaceutically acceptable salt thereof, and a suitable pharmaceutical vehicle.

9. A method of treating susceptible gram-positive infections which comprises administering an effective amount of a composition of claim 8 to an infected or susceptible warm-blooded animal.

10. A feed composition for increasing feed-utilization efficiency in animals which comprises (1) an effective amount of a compound of claim 1 or a pharmaceutically-acceptable salt thereof, and (2) a standard feed ration.

11. A method for increasing feed-utilization in animals which comprises administering an effective amount of a composition of claim 10 to the animal.

12. A feed composition for improving milk production in lactating ruminants comprising (1) an effective amount of a compound of claim 1, or a pharmaceutically acceptable salt thereof, and (2) a standard feed ration.

13. A method of improving milk production in lactating ruminants comprising orally administering an effective amount of a composition of claim 12 to the ruminant.

14. The method of claim 13 wherein the ruminant is a dairy cow.

* * * * *

UNITED STATES PATENT AND TRADEMARK OFFICE
CERTIFICATE OF CORRECTION

PATENT NO. : 4,563,442  
DATED : January 7, 1986  
INVENTOR(S) : Gladys M. Clem, LaVerne D. Boeck, Marie T. Anderson and Karl H. Michel Page 1 of 3

It is certified that error appears in the above—identified patent and that said Letters Patent is hereby corrected as shown below:

Column 2, that portion of the structural formula reading

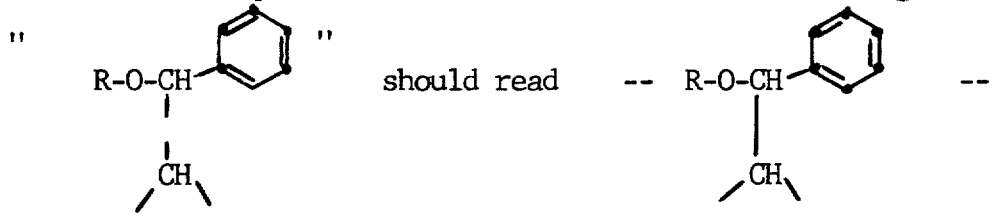

Column 2, that portion of the structural formula reading

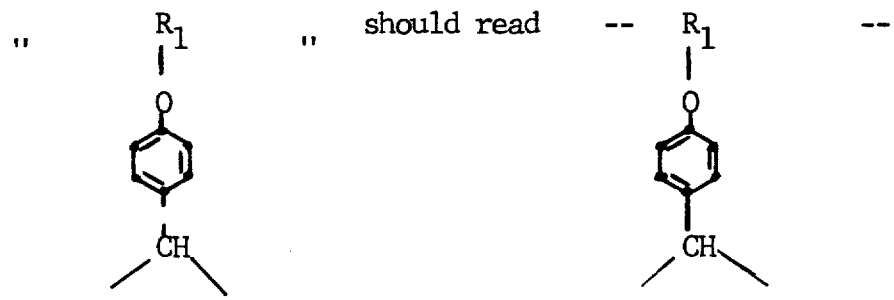

UNITED STATES PATENT AND TRADEMARK OFFICE
CERTIFICATE OF CORRECTION

PATENT NO. : 4,563,442  Page 2 of 3
DATED : January 7, 1986
INVENTOR(S) : Gladys M. Clem, LaVerne D. Boeck, Marie T. Anderson and Karl H. Michel It is certified that error appears in the above—identified patent and that said Letters Patent is hereby corrected as shown below:

Column 2, that portion of the structural formula reading

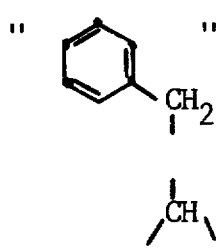  should read 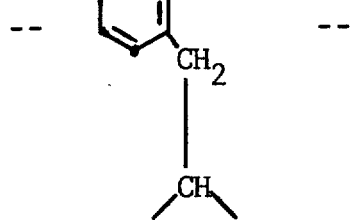

Column 6, after Table III insert -- [a]Administered subcutaneously 1 and 4 hours post-infection --.

Column 8, lines 34-38, delete beginning with "KCl" through "q.s. to 100%".

Column 8, line 40, insert below footnote "a" the following:

UNITED STATES PATENT AND TRADEMARK OFFICE
CERTIFICATE OF CORRECTION

PATENT NO. : 4,563,442         Page 3 of 3
DATED      : January 7, 1986
INVENTOR(S) : Gladys M. Clem, LaVerne D. Boeck, Marie T. Anderson and Karl H. Michel It is certified that error appears in the above—identified patent and that said Letters Patent is hereby corrected as shown below:

| Ingredient | Amount (%) |
|---|---|
| KCl | 10.0 |
| $MgSO_4 \cdot 7H_2O$ | 10.0 |
| $FeSO_4 \cdot 7H_2O$ | 0.2 (dissolved in 2 ml of Conc. HCl) |
| Deionized water | q.s. to 100% |

Column 9, line 30, "a pH" should read -- at pH --.

Signed and Sealed this

Nineteenth Day of August 1986

[SEAL]

Attest:

DONALD J. QUIGG

Attesting Officer

Commissioner of Patents and Trademarks